(12) United States Patent
Feke et al.

(10) Patent No.: US 9,113,784 B2
(45) Date of Patent: *Aug. 25, 2015

(54) APPARATUS AND METHOD FOR MULTI-MODAL IMAGING

(75) Inventors: Gilbert D. Feke, Durham, CT (US);
William E. McLaughlin, Guilford, CT (US); Douglas L. Vizard, Durham, CT (US)

(73) Assignee: Bruker Biospin Corporation, Billerica, MA (US)

( * ) Notice: Subject to any disclaimer, the term of this patent is extended or adjusted under 35 U.S.C. 154(b) by 593 days.

This patent is subject to a terminal disclaimer.

(21) Appl. No.: 13/238,290

(22) Filed: Sep. 21, 2011

(65) Prior Publication Data
US 2012/0008742 A1    Jan. 12, 2012

Related U.S. Application Data

(63) Continuation of application No. 12/763,231, filed on Apr. 20, 2010, now abandoned, which is a continuation-in-part of application No. 11/221,530, filed on Sep. 8, 2005, now Pat. No. 7,734,325, and a
(Continued)

(51) Int. Cl.
*A61B 6/00* (2006.01)
*A61B 5/00* (2006.01)

(52) U.S. Cl.
CPC .......... *A61B 5/0059* (2013.01); *A61B 6/00* (2013.01); *A61B 6/5247* (2013.01); *A61B 6/4417* (2013.01)

(58) Field of Classification Search
CPC ...... A61B 6/00; A61B 5/0059; A61B 6/4417; A61B 6/5247

USPC .............. 600/407; 250/339.06, 336.1, 367; 378/51
See application file for complete search history.

(56) References Cited

U.S. PATENT DOCUMENTS

| | | | |
|---|---|---|---|
| 1,609,703 | A | 12/1926 | Eggert et al. |
| 3,717,764 | A | 2/1973 | Fujimura et al. |
| 3,936,644 | A | 2/1976 | Rabatin |
| 4,028,550 | A | 6/1977 | Weiss et al. |
| 4,088,894 | A | 5/1978 | Rabatin |

(Continued)

FOREIGN PATENT DOCUMENTS

| | | |
|---|---|---|
| EP | 1 111 625 A2 | 6/2001 |
| EP | 1 304 070 A2 | 4/2003 |

(Continued)

OTHER PUBLICATIONS

Yamashita et al., Mist particle diameters are related to the toxicity of waterproofing sprays: Comparison between toxic and non-toxic products, Vet Human Toxicol., (2), vol. 39, Apr. 1997, pp. 71-74.

(Continued)

*Primary Examiner* — Vani Gupta
(74) *Attorney, Agent, or Firm* — O'Shea Getz P.C.

(57) ABSTRACT

An imaging system and method for imaging an immobilized object. The imaging system includes a support member adapted to receive the object in an immobilized state. The system also includes means for imaging the immobilized object in various imaging modes to capture images of the object. The imaging system further includes a movable phosphor screen. The phosphor screen is adapted to be movable without moving the immobilized object and support member.

6 Claims, 9 Drawing Sheets

Related U.S. Application Data continuation-in-part of application No. 12/196,300, filed on Aug. 22, 2008, now abandoned, and a continuation-in-part of application No. 12/354,830, filed on Jan. 16, 2009, now Pat. No. 8,050,735, and a continuation-in-part of application No. 12/381,599, filed on Mar. 13, 2009, now abandoned, and a continuation-in-part of application No. 12/475,623, filed on Jun. 1, 2009, now Pat. No. 8,660,631.

(56) References Cited

U.S. PATENT DOCUMENTS

| | | |
|---|---|---|
| 4,107,070 A | 8/1978 | Everts et al. |
| 4,208,470 A | 6/1980 | Rabatin |
| 4,232,227 A | 11/1980 | Finkenzeller et al. |
| 4,394,737 A | 7/1983 | Komaki et al. |
| 4,446,365 A | 5/1984 | Ong et al. |
| 4,675,529 A | 6/1987 | Kushida |
| 4,710,637 A | 12/1987 | Luckey et al. |
| 4,829,188 A | 5/1989 | Shinomiya et al. |
| 4,870,279 A | 9/1989 | Cueman et al. |
| 4,891,527 A | 1/1990 | Rabatin |
| 4,898,175 A | 2/1990 | Noguchi |
| 5,069,982 A | 12/1991 | Zegarski |
| 5,307,804 A | 5/1994 | Bonnet |
| 5,501,225 A | 3/1996 | Wilson |
| 5,517,193 A | 5/1996 | Allison et al. |
| 5,534,709 A | 7/1996 | Yoshimoto et al. |
| 5,650,135 A | 7/1997 | Contag et al. |
| 5,663,005 A | 9/1997 | Dooms et al. |
| 5,717,791 A | 2/1998 | Labaere et al. |
| 5,730,701 A | 3/1998 | Furukawa et al. |
| 5,748,768 A | 5/1998 | Sivers et al. |
| 5,830,629 A | 11/1998 | Vizard et al. |
| 6,216,540 B1 * | 4/2001 | Nelson et al. ............ 73/633 |
| 6,227,704 B1 | 5/2001 | Bani-Hashemi et al. |
| 6,229,873 B1 | 5/2001 | Bani-Hashemi et al. |
| 6,268,613 B1 | 7/2001 | Cantu et al. |
| 6,269,177 B1 | 7/2001 | Dewaele et al. |
| 6,278,765 B1 | 8/2001 | Berliner |
| 6,346,707 B1 | 2/2002 | Vizard et al. |
| 6,379,044 B1 | 4/2002 | Vastenaeken et al. |
| 6,416,800 B1 | 7/2002 | Weber et al. |
| 6,423,002 B1 | 7/2002 | Hossack |
| 6,424,750 B1 | 7/2002 | Colbeth et al. |
| 6,444,988 B1 | 9/2002 | Vizard |
| 6,447,163 B1 | 9/2002 | Bani-Hashemi et al. |
| 6,459,094 B1 | 10/2002 | Wang et al. |
| 6,473,489 B2 | 10/2002 | Bani-Hashemi et al. |
| 6,495,812 B1 | 12/2002 | Wurm et al. |
| 6,531,225 B1 | 3/2003 | Homme et al. |
| 6,615,063 B1 | 9/2003 | Ntziachristos et al. |
| 6,686,200 B1 | 2/2004 | Dong et al. |
| 6,762,420 B2 | 7/2004 | Homme et al. |
| 6,948,502 B2 | 9/2005 | Berger et al. |
| 7,113,217 B2 | 9/2006 | Nilson et al. |
| 7,190,991 B2 | 3/2007 | Cable et al. |
| 7,198,404 B2 | 4/2007 | Navab et al. |
| 7,338,651 B2 | 3/2008 | Bornhop et al. |
| 7,394,053 B2 | 7/2008 | Frangioni et al. |
| 7,406,967 B2 | 8/2008 | Callaway |
| 7,502,174 B2 | 3/2009 | Jensen et al. |
| 7,734,325 B2 | 6/2010 | Vizard et al. |
| 8,055,045 B2 | 11/2011 | Kokubun et al. |
| 2001/0012386 A1 | 8/2001 | Struye et al. |
| 2003/0011701 A1 | 1/2003 | Nilson et al. |
| 2003/0082104 A1 | 5/2003 | Mertelmeier |
| 2003/0187344 A1 | 10/2003 | Nilson et al. |
| 2003/0211158 A1 | 11/2003 | Frechet et al. |
| 2004/0004193 A1 | 1/2004 | Nilson et al. |
| 2004/0089817 A1 | 5/2004 | Long et al. |
| 2004/0199067 A1 | 10/2004 | Bock et al. |
| 2004/0202360 A1 | 10/2004 | Besson |
| 2004/0249260 A1 | 12/2004 | Wang et al. |
| 2005/0028482 A1 | 2/2005 | Cable et al. |
| 2005/0122529 A1 | 6/2005 | Kim et al. |
| 2005/0148846 A1 | 7/2005 | Cable et al. |
| 2005/0175538 A1 | 8/2005 | Coquoz et al. |
| 2005/0237423 A1 | 10/2005 | Nilson et al. |
| 2006/0064000 A1 | 3/2006 | Vizard et al. |
| 2006/0111613 A1 | 5/2006 | Boutillette et al. |
| 2006/0118742 A1 | 6/2006 | Levenson et al. |
| 2006/0173354 A1 | 8/2006 | Ntziachristos et al. |
| 2006/0210135 A1 | 9/2006 | Kanegae |
| 2006/0239398 A1 | 10/2006 | McCroskey et al. |
| 2006/0241402 A1 | 10/2006 | Ichihara et al. |
| 2007/0016077 A1 | 1/2007 | Nakaoka et al. |
| 2007/0063154 A1 | 3/2007 | Chen et al. |
| 2007/0087445 A1 | 4/2007 | Tearney et al. |
| 2007/0217713 A1 | 9/2007 | Milanfar et al. |
| 2007/0238957 A1 | 10/2007 | Yared |
| 2007/0281322 A1 | 12/2007 | Jaffe et al. |
| 2008/0045797 A1 | 2/2008 | Yasushi et al. |
| 2008/0049893 A1 | 2/2008 | Bartzke et al. |
| 2008/0197296 A1 | 8/2008 | Uematsu |
| 2008/0281322 A1 | 11/2008 | Sherman et al. |
| 2009/0086908 A1 | 4/2009 | Harder et al. |
| 2009/0116717 A1 | 5/2009 | Kohler et al. |
| 2009/0159805 A1 | 6/2009 | Feke et al. |
| 2009/0238434 A1 | 9/2009 | Feke et al. |
| 2010/0022866 A1 | 1/2010 | Feke et al. |

FOREIGN PATENT DOCUMENTS

| | | |
|---|---|---|
| EP | 1 619 548 A2 | 1/2006 |
| JP | 58-17544 U | 7/1981 |
| JP | 02-031144 | 2/1990 |
| JP | 02-052246 | 2/1990 |
| JP | 09-309845 | 12/1997 |
| JP | 11-244220 | 9/1999 |
| JP | 2001-255607 | 9/2001 |
| JP | 2001-299786 | 10/2001 |
| JP | 2003-028995 | 1/2003 |
| JP | 2004-121289 | 4/2004 |
| JP | 2005-049341 | 2/2005 |
| JP | 2005-164577 | 6/2005 |
| WO | 2004/081865 A2 | 9/2004 |
| WO | 2004/089204 A1 | 10/2004 |
| WO | 2004/108902 A2 | 12/2004 |
| WO | 2005/027730 A2 | 3/2005 |
| WO | 2007/032940 A2 | 3/2007 |

OTHER PUBLICATIONS

Research Takes Many Directions, *Science*, vol. 303, No. 5657, Jan. 23, 2004. Advertisement (2 pages).

Sage, Linda, "The Bare Bones of Animal Imaging", *The Scientist*, vol. 19, Issue 4, Feb. 28, 2005. (4 pages).

"Monomolecular Multimodal Fluorescence-Radiosotope Imaging Agents", Bioconjugate Chemistry, 16(5), pp. 1232-1239, 2005.

CosmoBio report, Mar. 2004, No. 43, "Kodak Image Station 2000MM". (English translation of p. 18—5 pages).

CosmoBio report, Mar. 2004, No. 43, "Kodak Image Station 2000MM". (JP language—Foreign, 13 pages).

Kodak Image Station 2000MM Multimodal Imaging System, Internet web address: http://www.kodak.com/US/en/health/scientific/products/imgstation2000MM/index.shtml—Sep. 16, 2004. (1 page).

Hussain et al., Enhanced Oral Uptake of Tomato Lectin-Conjugated Nanoparticles in the Rat, Pharmaceutical Research, vol. 14, No. 5, 1997, pp. 613-618.

V.P. Torchilin, Polymer-coated long-circulating microparticulate pharmaceuticals, J. Microencapsulation, 1998, vol. 15, No. 1, pp. 1-19.

Alyautdin et al., Delivery of Loperamide Across the Blood-Brain Barrier with Polysorbate 80-Coated Polybutylcyanoacrylate Nanoparticles, Pharmaceutical Research, vol. 14, No. 3, 1997, pp. 325-328.

Y. Kwon et al., Enhanced antigen presentation and immunostimulation of dendritic cells using acid-degradable cationic nanoparticles, Journal of Controlled Release 105, 2005, pp. 199-212.

(56) References Cited

OTHER PUBLICATIONS

Harlow et al., Antibodies—A Laboratory Manual, Chapter 5-Immunizations, 1988, pp. 91-113.
Winter et al., Man-made antibodies, Nature—vol. 349, Jan. 24, 1991, pp. 293-299.
Köhler et al., Derivation of specific antibody-producing tissue culture and tumor lines by cell fusion, Medical Research Council Laboratory of Molecular Biology, Cambridge, Eur. J. Immunol., 1976, vol. 6, pp. 511-519.
LoBuglio et al., Mouse/human chimeric conoclonal antibody in man: Kinetics and immune response, Proc. Natl. Acad. Sci., vol. 86, Jun. 1989 Immunology, pp. 4220-4224.
De Verdiè, et al., Reversion of multidrug resistence with polyalkycyanoacrylate nanoparticles: towards a mechanism of action, BJC British Journal of Cancer, 1997, vol. 76 (2), pp. 198-205.
Sharma et al., Novel Taxol® Formulation: Polyvinylpyrrolidone Nanoparticle-Encapsulated Taxol® for Drug Delivery in Cancer Therapy, Oncology Research, vol. 8, Nos. 7/8, pp. 281-286, 1986.
Zobel et al., Cationic Polyhexylcyanoacrylate Nanoparticles as Carriers for Antisense Oligonucleotides, Antisense & Nucleic Acid Drug Development, vol. 7, 1997, pp. 483-493.
Burke et al., Acid-Base Equilibria of Weak Polyelectrolytes in Multilayer Thin Films, Langmuir, 2003, vol. 19, No. 8, pp. 3297-3303.
Hrkach et al., Nanotechnology for biomaterials engineering; structural characterization of amphiphilic polymeric nanoparticles by $^1$H NMR spectroscopy, Biomaterials, vol. 18, No. 1, 1997, pp. 27-30.
G. Volkheimer, Übersicht, Persorption von Mikropartikeln, Pathologies, 1993, vol. 14, pp. 247-252.
Moghimi et al., Nanomedicine: current status and future prospects, The FASEB Journal, vol. 19, Mar. 2005, pp. 311-330.
Soukchareun et al., Preparation and Characterization of Antisense Oligonucleotide—Peptide Hybrids Containing Viral Fusion Peptides, Bioconjugate Chem, 1995, vol. 6, pp. 43-53.
G. Kwon et al., Block copolymer micelles as long-circulating drug vehicles, Advanced Drug Delivery Reviews, vol. 16, 1995, pp. 295-309.
Labhasetwar et al., Nanoparticle drug delivery system for restenosis, Advanced Drug Delivery Reviews, vol. 24, 1997, pp. 63-85.
Co-pending U.S. Appl. No. 11/400,935, filed Apr. 10, 2006, Publication No. 2000/0238656, Harder et al., Functionalized Poly(Ethylene Glycol).
Co-pending U.S. Appl. No. 11/165,849, filed Jun. 24, 2006, Publication No. 2006/0293396, Bringley et al., Nanoparticle Based Substrate for Image Contrast Agent Fabrication.
Yamashita et al., Mist particle diameters are related to the toxicity of waterproofing sprays: Comparison between toxic and non-toxic products, vol. 39, 71-74.
Cleare et al., "An Experimental Study of the Mottle Produced by X-Ray Intensifying Screens," The Am. J. of Roent. and Rad. Physics, vol. 88, No. 1, pp. 168-174, Jul. 1962.
Nature Methods, "Harnessing multimodality to enhance quantification and reproducibility of in vivo molecular imaging data", by Gilbert D. Feke et al., Nov. 2008, 2 pages.
Biochem Biophys Res Commun, Inspiration for Life Science, "Anti Human Galectin 3 Polyelonal Antibody", by W. Zhu, 280:11831188, 2001, 2 pages.
IEEE Transactions on Nuclear Science, "Iodine 125 Imaging in Mice Using NaI(TI)/Flat Panel PMT Integral Assembly", by M.N. Cinti et al., vol. 54, No. 3, Jun. 2007, pp. 461-468.
Mat. Res. Soc. Symp. Proc., "Optimising of the Physico-Chemical Properties of a Novel Barium Sulphate Preparation for the X-Ray Examination of the Intestine", by Barbara Laermann et al., vol. 550, 1999 Materials Research Society, pp. 59-64.
Am. Assoc. Phys. Med., "MicroCT scanner performance and considerations for vascular specimen imaging", by Michael Marxen et al., Med. Phys. 31 (2), Feb. 2004, pp. 305-313.
Rat Atlas Project, Internet Study: Hubei Bioinformatics and Molecular Imaging Key Laboratory, The Key Laboratory of Biomedical Photonics of Ministry of Education, College of Life Science and Technology, Huazhong University of Science and Technology, http://www.vch.org.cn/mice/method.aspx , printed from Internet on Sep. 12, 2011, (4 pages).
Kodak Image Station 2000MM Multi-Modal Imager, Kodak Scientific Imaging Systems—advertisement—Fall/2003 (2 pages).
Proceedings of the American Thoracic Society, "Micro-Computed Tomography of the Lungs and Pulmonary-Vascular System", by Erik L. Ritman, 2 pp. 477-480, 2005.
The Journal of Nuclear Medicine, "Significance of Incidental 18F-FDG Accumulations in the Gastrointestical Tract in PET/CT: Correlation with Endoscopic and Histopathologic Results", by Ehab M. Kamel et al., vol. 45, No. 11, pp. 1804-1810, 2004.
P. Mitchell, "Picture Perfect: Imaging Gives Biomarkers New Look", *Pharma DD*, vol. 1, No. 3, pp. 1-5 (2006).
Virostko et al., Molecular Imaging, vol. 3, No. 4, Oct. 2004, pp. 333-342, Factors Influencing Quantification of In Vivo Bioluminescence Imaging: Application to Assessment of Pancreatic Islet Transplants.
Da Silva et al., ScienceDirect, Nuclear Instruments and Methods in Physics Research, Design of a small animal multimodality tomographer for X-ray and optical coupling: Theory and experiments, 2007, pp. 118-121.
Kruger et al., HYPR-spectral photoacoustic CT for preclinical imaging, Photons Plus Ultrasound Imaging and Sensing 2009, Proc. of SPIE, vol. 7177, 10 pages.
User's Guide for Kodak Image Station 2000R, Aug. 2002, (172 Pages).
User's Guide for Kodak Image Station 2000MM, Nov. 2003 (168 Pages).
Corresponding WO = PCT/us2005/032504, International Preliminary Report on Patentability, dated Mar. 27, 2007, 8 pages.
Corresponding CN = CN 200580031808.5—SIPO First Office Action dated Dec. 4, 2009. 14 pages.
International Search Report, International Application No. PCT/US2005/032504, dated Dec. 23, 2005, 10 pages.
International Search Report, International Application No. PCT/US2008/010304, dated Dec. 8, 2008, 5 pages.
International Search Report, International Application No. PCT/US2009/000457, dated Aug. 21, 2009, 3 pages.
Hamamatsu Photonics K.K., Catalog No. SFAS0017E06, X-Ray Line Scan Camera, Jun. 2010, 4 pages.
Hamamatsu Photonics K.K., Publication No. TMCP1031E04, X-Ray Scinitllator, Jun. 2009, 4 pages.
European Search Report dated Apr. 8, 2011 for European Application No. 10 01 2074.0, 2 pages.

* cited by examiner

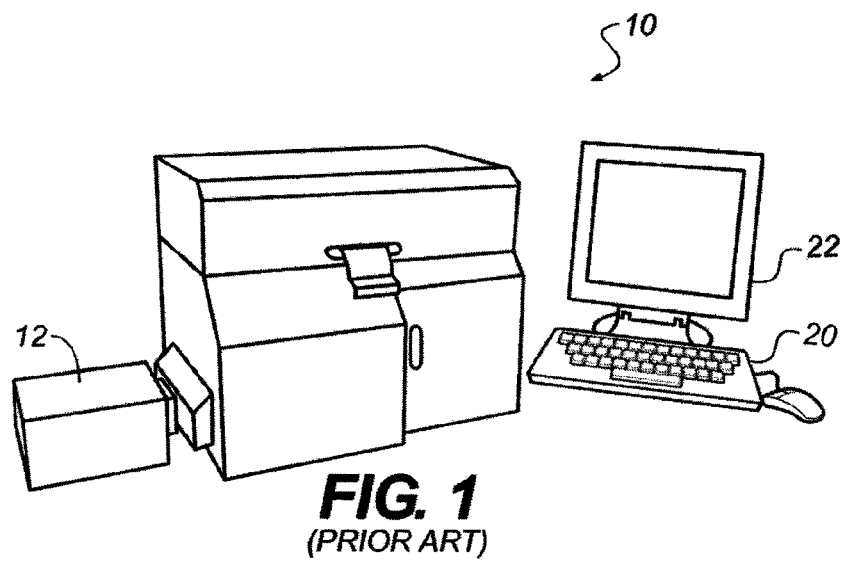
FIG. 1
(PRIOR ART)
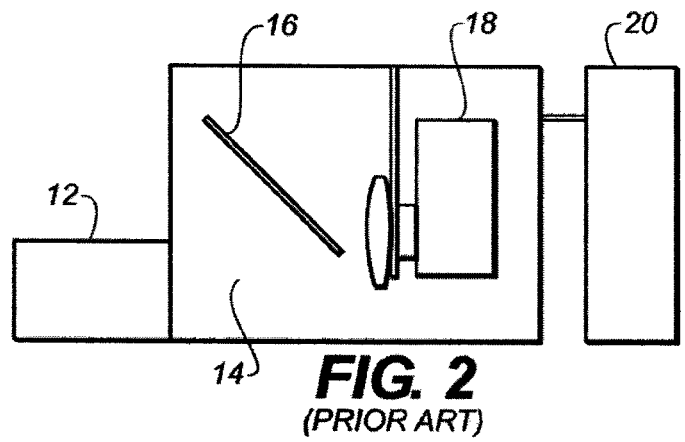
FIG. 2
(PRIOR ART)
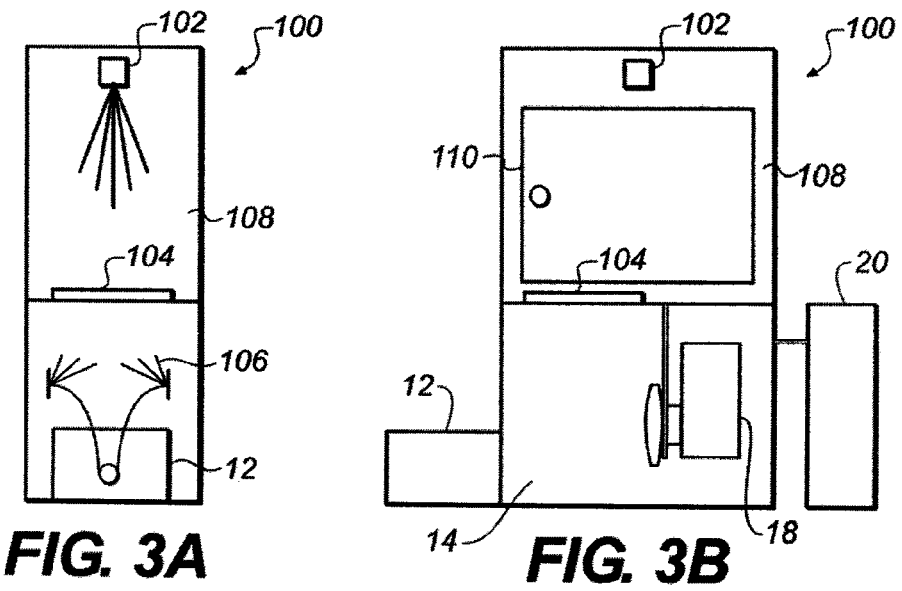
FIG. 3A  FIG. 3B

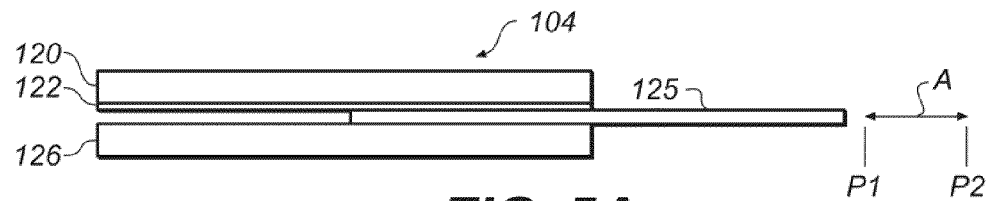
*FIG. 5A*
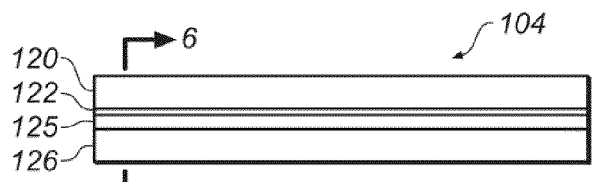
*FIG. 5B*
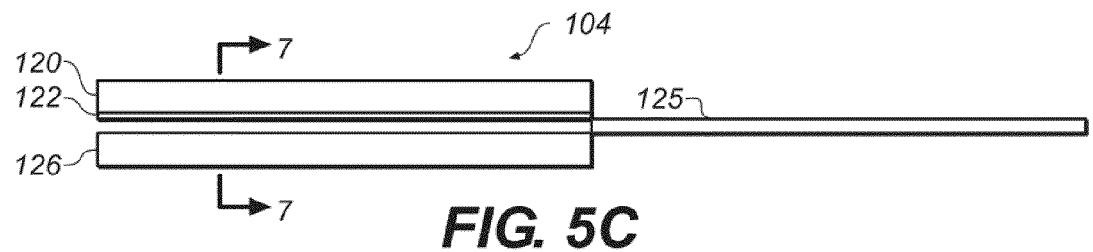
*FIG. 5C*
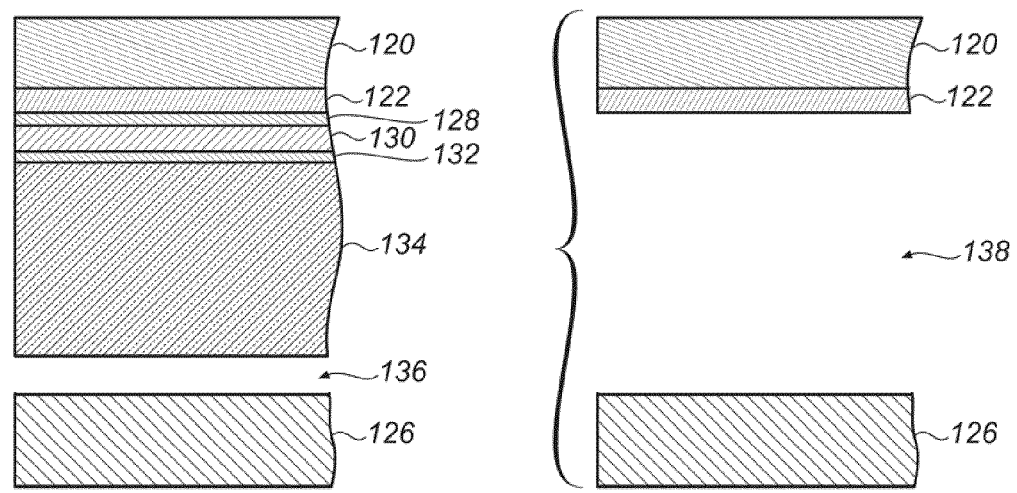
*FIG. 6*     *FIG. 7*

APPARATUS AND METHOD FOR MULTI-MODAL IMAGING

CROSS REFERENCE TO RELATED APPLICATIONS

This application is a continuation of U.S. Ser. No. 12/763,231 filed Apr. 20, 2010 now abandoned by Feke, entitled APPARATUS AND METHOD FOR MULTI-MODAL IMAGING, published as US 2010/0220836, which is incorporated by reference in its entirety.

The above-identified application was itself a continuation-in-part of the following commonly assigned, copending U.S. Patent Applications, each of which is incorporated by reference into this specification:

U.S. Ser. No. 11/221,530 filed Sep. 8, 2005 now U.S. Pat. No. 7,734,325 by Vizard et al, entitled APPARATUS AND METHOD FOR MULTI-MODAL IMAGING, published as US 2006/0064000;

U.S. Ser. No. 12/196,300 filed Aug. 22, 2008 now abandoned by Harder et al, entitled APPARATUS AND METHOD FOR MULTI-MODAL IMAGING USING NANOPARTICLE MULTI-MODAL IMAGING PROBES, published as US 2009/0086908;

U.S. Ser. No. 12/354,830 filed Jan. 16, 2009 now U.S. Pat. No. 8,050,735 by Feke et al, entitled APPARATUS AND METHOD FOR MULTI-MODAL IMAGING, published as US 2009/0159805;

U.S. Ser. No. 12/381,599 filed Mar. 13, 2009 now abandoned by Feke et al, entitled METHOD FOR REPRODUCING THE SPATIAL ORIENTATION OF AN IMMOBILIZED SUBJECT IN A MULTI-MODAL IMAGING SYSTEM, published as US 2009/0238434; and U.S. Ser. No. 12/475,623 filed Jun. 1, 2009 now U.S. Pat. No. 8,660,631 by Feke et al, entitled TORSIONAL SUPPORT APPARATUS AND METHOD FOR CRANIOCAUDAL ROTATION OF ANIMALS, published as US 2010/0022866.

FIELD OF THE INVENTION

The invention relates generally to the field of imaging systems, and more particularly to the imaging of objects. More specifically, the invention relates to an apparatus and method that enable analytical imaging of objects (for example, small animals and tissue) in differing modes, including bright-field, dark-field (e.g., luminescence and fluorescence), and x-ray and radioactive isotopes.

BACKGROUND OF THE INVENTION

Electronic imaging systems are well known for enabling molecular imaging. An exemplary electronic imaging system (shown in FIG. 1 and diagrammatically illustrated in FIG. 2) is the Image Station 2000MM Multimodal Imaging System 10 available from the Eastman Kodak Company. System 10 includes a light source 12, an optical compartment 14 which can include a mirror 16, a lens/camera system 18, and a communication/computer control system 20 which can include a display device, for example, a computer monitor 22. Camera/lens system 18 can include an emission filter wheel for fluorescent imaging. Light source 12 can include an excitation filter selector for fluorescent excitation or bright field color imaging. In operation, an image of an object is captured using lens/camera system 18. System 18 converts the light image into an electronic image, which can be digitized. The digitized image can be displayed on the display device, stored in memory, transmitted to a remote location, processed to enhance the image, and/or used to print a permanent copy of the image.

Applicants have recognized a need for an apparatus and method for enabling analytical imaging of an object in differing modes.

SUMMARY OF THE INVENTION

An object of the present invention is to provide an apparatus and method for enabling analytical imaging of an object. Another object of the present invention is to provide such an apparatus and method for enabling analytical imaging of an object in differing modes.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

One embodiment of the invention concerns an imaging system for imaging an immobilized object. The system includes a support member adapted to receive the object in an immobilized state, the support member including a frame supporting an optically clear support element for the object. An imaging unit is included for imaging the immobilized object in a first imaging mode to capture a first image, the first imaging mode being selected from the group consisting of: x-ray mode and radio isotope mode; and for imaging the immobilized object in a second imaging mode that uses light from the immobilized object, different from the first imaging mode, to capture a second image, the second imaging mode being selected from the group consisting of: bright-field mode, fluorescence mode, and luminescence mode. A movable phosphor plate is included to transduce ionizing radiation to visible light. The phosphor plate is mounted to be moved, without moving the immobilized object and the support member, between a first position proximate the support member for and during capture of the first image and a second position not proximate the support member during capture of the second image. A layer on the phosphor plate protects a surface of the phosphor plate facing the support element of the support member during movement of the phosphor plate between the first and second positions. A capture system is included for capturing either the first image or the second image of the object.

Another embodiment of the invention also concerns an imaging system for imaging an immobilized object. A support member is adapted to receive the object in an immobilized state. An imaging unit is included for imaging the immobilized object in a first imaging mode to capture a first image, the first imaging mode being selected from the group consisting of: x-ray imaging mode and isotope imaging mode; and for imaging the immobilized object in a second imaging mode that uses light from the object to capture a second image, the second imaging mode being selected from the group consisting of: bright-field imaging mode and dark-field imaging mode. A movable phosphor plate is mounted to be disposed in a first position proximate the support member when capturing the first image. A moving unit is provided for removing the phosphor plate from the first position proximate the support member, after capturing the first image and without moving the immobilized object and the support member, and for moving the phosphor plate to a second position not proximate the support member prior to capturing the second image. A capture system is provided for capturing either the first image or the second image of the object, the capture system comprising a camera, a first mirror on a first side of the support member for reflecting to the camera light from the object or from the phosphor plate to capture the first and second images; and a second mirror on a second, opposite side of the support member for reflecting to the camera light to capture a third image from an opposite side of the object than that of the second image.

Yet another embodiment of the invention concerns a method of imaging an immobilized object. The method includes steps of providing a support member adapted to receive the object in an immobilized state; placing the object on the support member in an immobilized state; providing a phosphor plate adapted to be disposed proximate the support member when capturing a first image; disposing the phosphor plate proximate the support member; imaging the immobilized object in a first imaging mode to capture the first image, the first imaging mode being selected from the group consisting of: x-ray mode and radio isotope mode; removing the phosphor plate from proximate the support member, after capturing the first image and without moving the immobilized object and the support member; with the phosphor plate removed from proximate the support member, imaging the immobilized object in a second imaging mode that uses light from the object to capture a second image, the second imaging mode being selected from the group consisting of bright-field mode and dark-field mode; and imaging the immobilized object in the second imaging mode, but from a side of the object opposite that used when capturing the second image, to capture a third image.

A further embodiment of the invention also concerns a method of imaging an immobilized object. The method includes steps of providing a support member adapted to receive the object in an immobilized state; placing the object on the support member in an immobilized state; providing a phosphor plate movable relative to the support member, without moving the immobilized object and the support member, between a first position wherein the phosphor plate is in optical registration with the support member and a second position wherein the phosphor plate is not in optical registration with the support member; disposing the phosphor plate in the first position; capturing a first, x-ray image or a first, radio isotopic image of the immobilized object when the phosphor plate is disposed in the first position; moving the phosphor plate to the second position; using light from the object, capturing a second, dark-field image or a second, bright-field image of the immobilized object when the phosphor plate is disposed in the second position; and using light from the object, capturing a third, dark-field image or a third, bright-field image of the immobilized object from a side of the object opposite that used during capture of the second, dark-field image or the second, bright-field image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1 shows a perspective view of an exemplary prior art electronic imaging system.

FIG. 2 shows a diagrammatic view of the prior art electronic imaging system of FIG. 1.

FIG. 3A shows a diagrammatic side view of the imaging system in accordance with the present invention.

FIG. 3B shows a diagrammatic front view of the imaging system of FIG. 3A.

FIG. 5A shows a diagrammatic side view of the sample object stage.

FIG. 5B shows a diagrammatic side view of the sample object stage in the first imaging position P1 wherein the phosphor plate is disposed proximate the sample object stage.

FIG. 5C shows a diagrammatic side view of the sample object stage in the second imaging position P2 wherein the phosphor plate is not proximate the sample object stage.

FIG. 6 shows an enlarged, fragmentary sectional view taken along line 6-6 of FIG. 5B.

FIG. 7 shows an enlarged, fragmentary sectional view taken along line 7-7 of FIG. 5C.

DETAILED DESCRIPTION OF THE INVENTION

Figure 4:
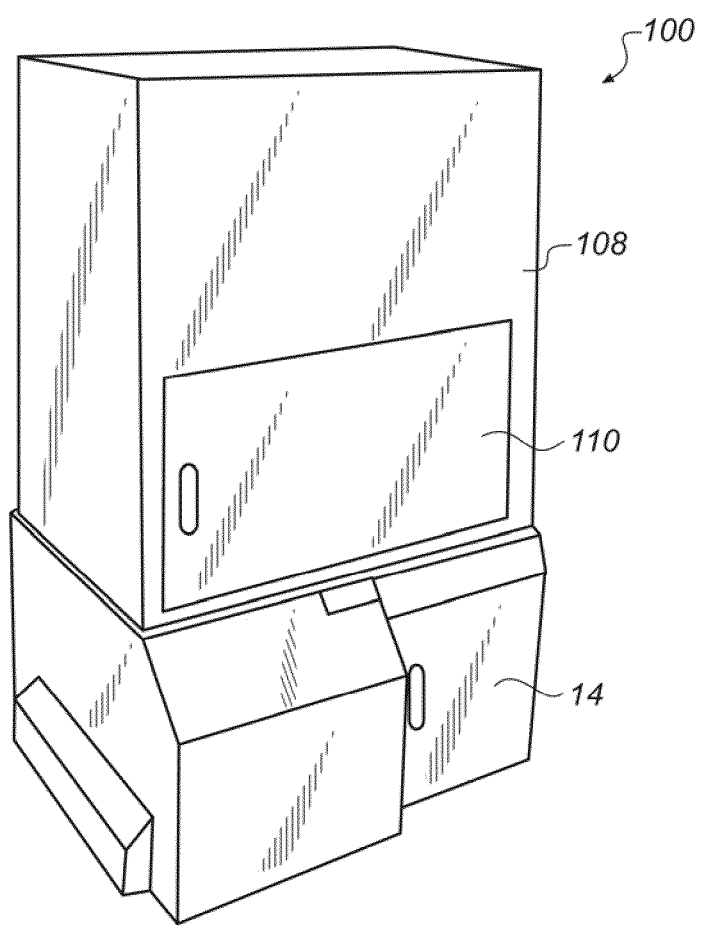
FIG. 4 shows a perspective view of the imaging system of FIGS. 3A and 3B.

The following is a detailed description of the preferred embodiments of the invention, reference being made to the drawings in which the same reference numerals identify the same elements of structure in each of the several figures.

Applicants have recognized that the complex pharmaceutical analyses of small objects/subjects (e.g., small animal and tissue) images are particularly enhanced by using different in-vivo imaging modalities. Using the known/current practices of bright-field, dark-field and radiographic imaging for the analysis of small objects/subjects (such as a mouse) can be expensive and may not provide the precision of co-registered images that is desired.

Using the apparatus and method of the present invention, precisely co-registered fluorescent, luminescent and/or isotopic probes within an object (e.g., a live animal and tissue) can be localized and multiple images can be accurately overlaid onto the simple bright-field reflected image or anatomical x-ray of the same animal within minutes of animal immobilization.

The present invention uses the same imaging system to capture differing modes of imaging, thereby enabling/simplifying multi-modal imaging. In addition, the relative movement of probes can be kinetically resolved over the time period that the animal is effectively immobilized (which can be tens of minutes). Alternatively, the same animal may be subject to repeated complete image analysis over a period of days/weeks required to assure completion of a pharmaceutical study, with the assurance that the precise anatomical frame of reference (particularly, the x-ray) may be readily reproduced upon repositioning the object animal. The method of the present invention can be applied to other objects and/or complex systems subject to simple planar imaging methodologies.

More particularly, using the imaging system of the present invention, an immobilized object can be imaged in several imaging modes without changing/moving the immobilized object. These acquired multi-modal images can then be merged to provide one or more co-registered images for analysis.

Imaging modes supported by the apparatus/method of the present invention include: x-ray imaging, bright-field imaging, dark-field imaging (including luminescence imaging, fluorescence imaging) and radioactive isotope imaging. Images acquired in these modes can be merged in various combinations for analysis. For example, an x-ray image of the object can be merged with a near IR fluorescence image of the object to provide a new image for analysis.

The apparatus of the present invention is now described with reference to FIGS. 3A, 3B, and 4. FIG. 3A shows a diagrammatic side view of an imaging system 100 in accordance with the present invention, FIG. 3B shows a diagrammatic front view of imaging system 100, and FIG. 4 shows a perspective view of imaging system 100.

Imaging system 100 includes light source 12, optical compartment 14, a lens/camera system 18, and communication/computer control system 20 which can include a display device, for example, a computer monitor 22. Camera/lens system 18 can include an emission filter wheel for fluorescent imaging. Light source 12 can include an excitation filter selector for fluorescent excitation or bright field color imaging.

As best shown in FIG. 3A, imaging system 100 includes an x-ray source 102 and a support member such as a sample object stage 104. An immobilized object such as a mouse is received on and supported by sample object stage 104 during operation of system 100 Imaging system 100 further comprises epi-illumination, for example, using fiber optics 106, which directs conditioned light (of appropriate wavelength and divergence) toward sample object stage 104 to provide bright-field or fluorescent imaging.

Sample object stage 104 is disposed within a sample environment 108, which allows access to the object being imaged. Preferably, sample environment 108 is light-tight and fitted with light-locked gas ports (not illustrated) for environmental control. Environmental control enables practical x-ray contrast below 8 Kev (air absorption) and aids in life support for biological specimens. Such environmental control might be desirable for controlled x-ray imaging or for support of particular specimens.

Imaging system 100 can include an access means/member 110 to provide convenient, safe and light-tight access to sample environment 108, such as a door, opening, labyrinth, and the like. Additionally, sample environment 108 is preferably adapted to provide atmospheric control for sample maintenance or soft x-ray transmission (e.g., temperature/humidity/alternative gases and the like).

Imaging system 100 can be a unitary system. Alternatively, imaging system 100 can be a modular unit adapted to be used/mated with electronic imaging system such as electronic imaging system 10.

FIGS. 5-7 more particularly illustrate elements of sample object stage 104 and an optical interface relative with the focal plane of camera/lens system 18. FIG. 5A shows a diagrammatic side view of sample object stage 104 showing the relative movement of a movable phosphor plate 125 according to the invention relative to the sample object stage. FIG. 5B shows a diagrammatic side view of the sample object stage in a first imaging position P1 wherein the phosphor plate 125 is disposed proximate the sample object stage and positioned for imaging light from a phosphor layer 130, shown in FIG. 6. FIG. 5C shows a diagrammatic side view of the sample object stage in the second imaging position P2 wherein phosphor plate 125 has been withdrawn to a position that is not proximate the sample object stage. FIG. 6 shows an enlarged, fragmentary sectional view taken along line 6-6 of FIG. 5B, which corresponds with the first imaging position P1. FIG. 7 shows an enlarged, fragmentary sectional view taken along line 7-7 of FIG. 5C, which corresponds with the second imaging position P2.

Continuing with regard to FIGS. 6 and 7, sample object stage 104 includes a support member made up from an open frame 120 to support and stretch a thin plastic support sheet 122. Support sheet 122 is selected so as to support the weight of a sample or object to be imaged and is made from a material that is optically clear and free of significant interfering fluorescence.

Phosphor plate 125 is mounted for motion toward and away from sample object stage 104. While those skilled in the art might recognize other configurations, in a preferred embodiment, phosphor plate 125 is mounted for translation to provide slidable motion (in the direction of arrow A in FIG. 5A) relative to frame 120, beneath the sample, in intimate contact with support sheet 122. Such motion can be accomplished using methods known to those skilled in the art, for example, frame 100 and phosphor plate 125 can be disposed on rails supported by a surface of an optical platen 126. As will be more particularly described below, in a first imaging position P1, phosphor layer 130 in phosphor plate 125 is in overlapping arrangement with sample object stage 104 (FIG. 6) when an x-ray image of the object is captured. In second imaging position P2, phosphor plate 125 is translated/moved away from sample object stage 104 (FIG. 7) for capture of an image of the object such that phosphor plate 125 is not imaged when an image of the object is captured in second imaging position P2.

FIG. 6 provides an enlarged view of sample object stage 104 including phosphor plate 125 to more particularly show a focal plane. Sample support sheet 122 preferably comprises Mylar or polycarbonate and has a nominal thickness of about 0.1 mm. A protective layer 128 (for example, reflective Mylar) of about 0.025 mm is provided to protect the phosphor surface of phosphor plate 125. Protective layer 128 promotes/increases the image-forming light output. In a preferred embodiment, protective layer 128 is reflective so as to prevent object reflection back into the image-forming screen, reducing the confusing the ionizing radiation image.

Phosphor layer 130 functions to transduce ionizing radiation to visible light that can be practically managed by lens and camera system 18 (such as a CCD camera). Phosphor layer 130 can have a thickness ranging from about 0.01 mm to about 0.1 mm, depending upon the application (i.e., soft x-ray, gamma-ray or fast electron imaging). On the underside of phosphor layer 130, as illustrated, an optical layer 132 is provided for conditioning emitted light from phosphor layer 130. Optical layer 132 can have a thickness in the range of less than about 0.001 mm. Particular information about phosphor layer 130 and optical layer 132 are disclosed in U.S. Pat. No. 6,444,988 (Vizard), commonly assigned and incorporated herein by reference. A supporting glass plate 134 is provided. Glass plate 134 is spaced at a suitable mechanical clearance from an optical platen 126, for example, by an air gap/void 136. In the preferred embodiment, the surfaces of clear optical media (e.g., a lower surface of glass plate 134 and both surfaces of optical platen 126) are provided with an antireflective coating to minimize reflections that may confuse the image of the object.

FIG. 7 provides an expanded view of sample object stage 104 including wherein phosphor plate 125 is removed (i.e., taken along line 7-7 of FIG. 5C). As shown in FIG. 7 is frame 120, sample support sheet 122, an air gap/void 138 (since phosphor plate 125 is removed), and optical platen 126.

Figure 8:
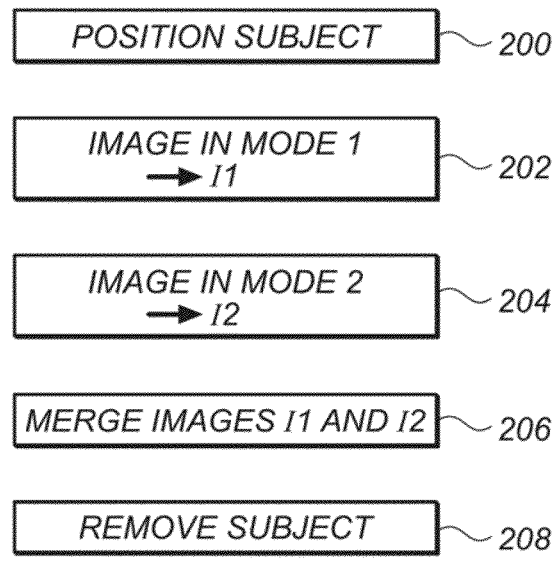
FIG. 8 shows a work flow diagram in accordance with a method of the present invention.

Referring now to FIG. 8, in operation, an object (such as a small animal) is immobilized on sample object stage 104 (step 200). An operator configures system 100 for imaging in a first mode, and an image of the object is captured using lens/camera system 18 in the first mode (step 202). System 18 converts the light image into an electronic image which can be digitized. This digitized image is referred to as Image1 or I1. The digitized image can be displayed on the display device, stored in memory, transmitted to a remote location, processed to enhance the image, and/or used to print a permanent copy of the image. The object remains immobilized on sample object stage 104; no change in the position/location of the object is made. The operator configures system 100 for imaging in a second mode (step 204), and an image of the object is captured using lens/camera system 18 in the second mode. The resulting digitized image is referred to as Image2 or I2. Since the position of the object was not moved/changed during the capture of the images, both Image1 and Image2 can readily be merged or superimposed (step 206), using methods known to those skilled in the art, such that the two images are co-registered. As such, a third image can be generated comprising Image1 and Image2. Once imaging is complete, the object/subject is removed from the sample stage (step 208).

As indicated above, system 100 can be configured in several modes, including: x-ray imaging, bright-field imaging, dark-field imaging (including luminescence imaging, fluorescence imaging) and radioactive isotope imaging. To configure system 100 for x-ray imaging or isotope imaging, phosphor plate 125 is moved to position P1 in optical registration with sample object stage 104 (as shown in FIGS. 5B and 6). For an x-ray image, x-ray source 102 is employed when capturing the image of the immobilized object. To configure system 100 for bright-field imaging or dark-field imaging (including luminescence imaging and fluorescence imaging) without moving the immobilized object and the support member or object stage, phosphor plate 125 is moved to position P2, out of optical registration with sample object stage 104 (as shown in FIGS. 5C and 7), and an image of the immobilized object is appropriately captured. The object is immobilized on sample object stage 104, and light emitted from the object (usually diffusive within the turbid constituents of a solid object) is projected to the object surface, which intimately bears upon the upper surface of sample support sheet 122.

For the purpose of optical imaging, the object surface is defined by a refractive boundary (e.g., the skin of an animal) that delineates the interior of the object (usually a heterogeneous, turbid media of higher index of refraction) and air. Light emanating from within an object (e.g., luminescent or transmitted) projects to the surface from which it scatters, defining the light that may be productively managed to create an image of the object. Conversely, light may be provided from beneath optical platen 126 and scattered from the object surface, thereby providing reflective light for imaging the same object.

For optical imaging, the definition of the object boundary may be moderated by matching the refractive index of the object boundary to support sheet 122 by introducing an index-matching fluid (e.g., water). The depth to which good focus can be achieved in optical imaging is dependent on minimizing the surface scatter of the object, and methods such as index matching and increasing wavelength (e.g., near-infrared, NIR imaging) are well known in the art.

The emitted sample light can arise from luminescence, fluorescence or reflection, and the focal plane of the lens can be adjusted to the elevation of object surface. Alternatively, the "light" can be ionizing radiation passing through or emitted from the object, or passing into the phosphor and forming an image. Soft x-rays, consistent with thin objects or small animals, project an image through the diffusive phosphor onto the optical boundary, adding the depth of the (more than about 0.02 mm) to the depth of focus. More significant is the focal distance contributed by the phosphor support plate 134, which may be fractional millimeters, depending upon the thickness and index of the glass or plastic. The fractional-millimeter elevation of the best focal plane contributed by the phosphor support can provide a better coincidence between the phosphor focal plane and the focal plane used for optical imaging. For near infrared (NIR) optical imaging, the preferred/best focal plane may be located at millimeter depths into a nominally turbid object. The phosphor support plate 134 can be thicker to maximize the coincidence of the optical and phosphor imaging planes. Those skilled in the art will recognize how to tune the materials of the present invention to optimally co-locate the preferred optical and phosphor imaging planes. Currently described materials may be practically assembled to assure multi-modal focal plane co-location to accommodate the demands of a fast lens system.

Appropriately fast lens systems for dark-field and x-ray imaging applications will likely have sub-millimeter focal depths, necessitating the above considerations. Accordingly, for a particular embodiment, it may be desirable for multiple optical elements to enable the location of a common focal plane shared by differing modes of imaging.

Emitted gamma rays from a thick object (such as 99Tc emission from an animal organ) are distributed over the plane of the phosphor, diffusing the image by millimeters, and an appropriately thick phosphor layer (about 0.1 mm) may be preferred for increased detection efficiency. Consequently, the location of the focal plane at the supporting sheet is not critical to the resolution of the radio isotopic image. Better resolution and more precise planar projection of the emitting isotope can be achieved by gamma-ray collimation. Collimators of millimeter-resolution are available and capable of projecting isotopic location to millimeter resolution at the focal plane of the phosphor in the present invention.

Of particular relevance to the operation of the present invention is the thickness of the layers in the focal plane of the lens. For example, fast lenses, (which are essential elements for the practice of imaging low-light emissions) will have a focal depth of focus of about 0.5 mm for very fast lenses. For good resolution of objects of interest, less than about 0.2 mm of spatial resolution is desirable, and a megapixel CCD camera (cooled) imaging at 100 mm field is suitable. Generally, more resolution is desirable.

Precision registration of the multi-modal image can be accomplished using methods known to those skilled in the art. By placing the object on a thin, stretched optical support that allows phosphor plate 125 to be removed without displacement of the object, co-registered optical imaging is enabled by the same lens/camera system using epi-illumination methodologies at a sufficiently similar focal plane.

Examples are now provided.

Figure 9A:
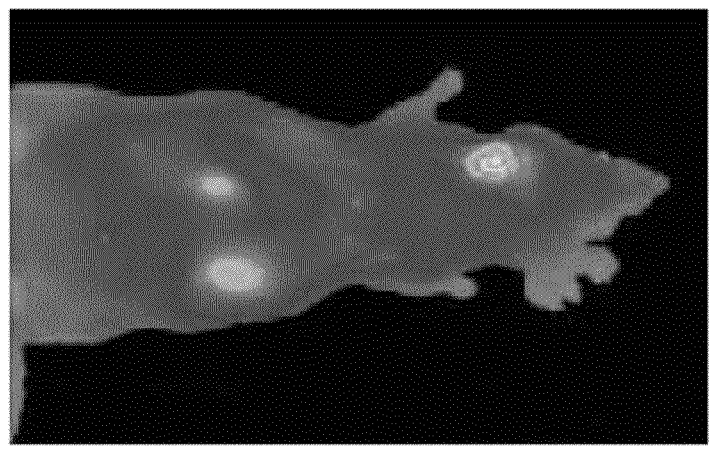
FIG. 9A shows a first image of an immobilized object in a first imaging mode.
Figure 9B:
FIG. 9B shows a second image of the immobilized object of FIG. 9A in a second imaging mode.
Figure 9C:
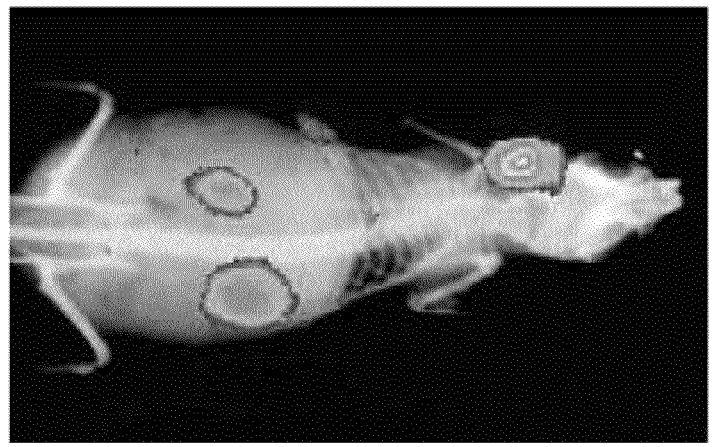
FIG. 9C shows an image generated by the merger of the images of FIGS. 9A and 9B.

FIGS. 9A-9C show images captured using the apparatus and method of the present invention. A mouse was immobilized on sample object stage 104 (step 200 of FIG. 8) of system 100. System 100 was first configured for NIR fluorescence imaging wherein phosphor plate 125 is removed from co-registration with frame 100. A first image was captured and is displayed in FIG. 9A (step 202 of FIG. 8). Next, system 100 was configured for x-ray imaging wherein phosphor plate 125 is placed in co-registration with frame 100. A second image was captured and is displayed in FIG. 9B (step 204 of FIG. 8). Using methods known to those skilled in the art, the first and second images were merged (step 206 of FIG. 8) and the merged image is displayed in FIG. 9C. Note that the fluorescent signals superimposed on the anatomical reference clarify the assignment of signal to the bladder and an expected tumor in the neck area of this illustrated experimental mouse.

It is noted that the first and/or second image can be enhanced using known image processing methods/means prior to be merged together. Alternatively, the merged image can be enhanced using known image processing methods/means. Often, false color is used to distinguish fluorescent signal from gray-scale x-rays in a merged image.

Figure 10C:
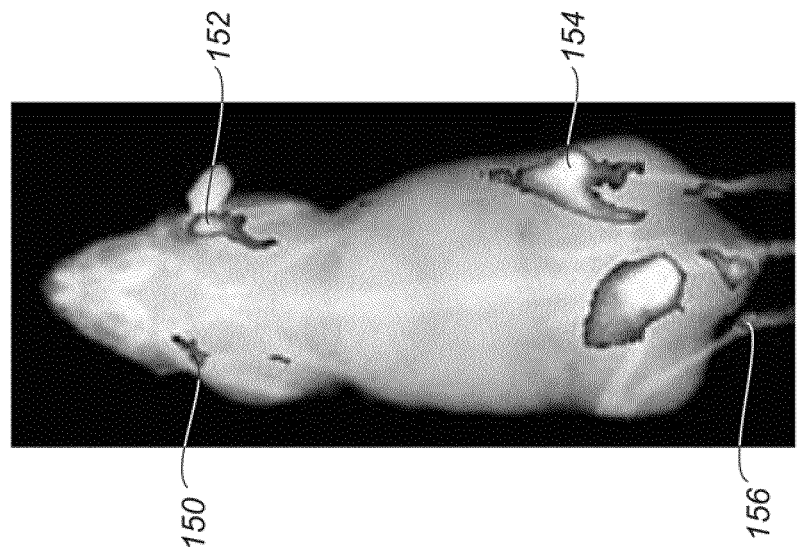
FIG. 10C shows an image generated by the merger of the images of FIGS. 10A and 10B.
Figure 10B:
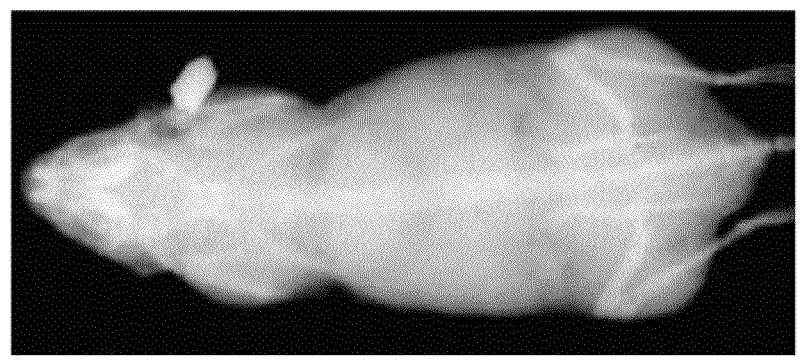
FIG. 10B shows a second image of the immobilized object of FIG. 10A in a second imaging mode.
Figure 10A:
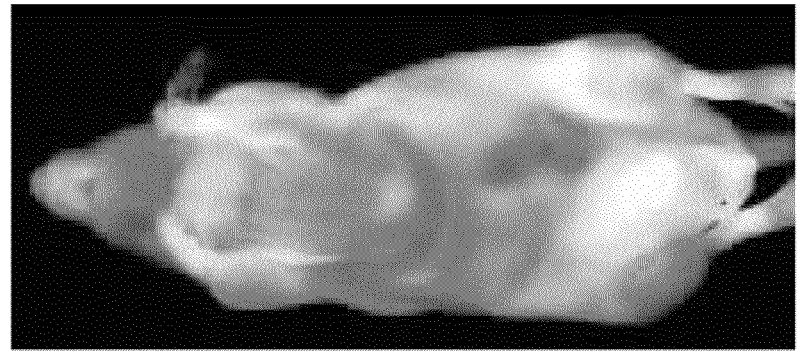
FIG. 10A shows a first image of an immobilized object in a first imaging mode.

FIGS. 10A-10C provide a further example using the apparatus and method of the present invention. FIG. 10A is a NIR fluorescence image of a mouse while FIG. 10B is an x-ray image of the same immobilized mouse. Using methods known to those skilled in the art, the first and second images were merged and the merged image is displayed in FIG. 10C. Prior to being merged, the first and second images were contrasted. This processing allows particular areas of the mouse to be visually enhanced for diagnostic purposes. For example, areas 150,152, and 156 are potential secondary early detection sites, and area 154 shows the primary tumor injection site at the knee.

Figure 11C:
FIG. 11C shows an image generated by the merger of the images of FIGS. 11A and 11B.
Figure 11B:
FIG. 11B shows a second image of the immobilized object of FIG. 11A in a second imaging mode.
Figure 11A:
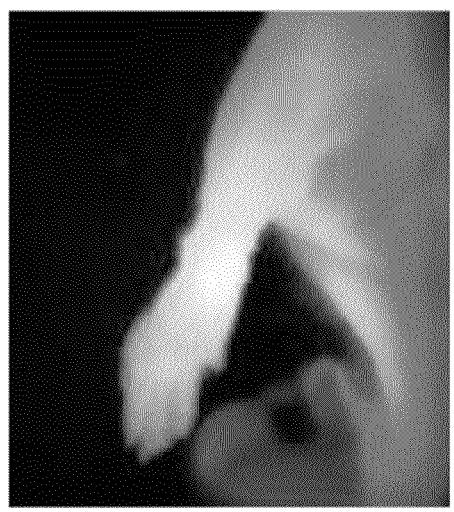
FIG. 11A shows a first image of an immobilized object in a first imaging mode.

FIGS. 11A-11C provide yet a further example using the apparatus and method of the present invention. FIG. 11A is a near IR fluorescence image of a mouse wrist while FIG. 11B is an x-ray image of the same immobilized mouse wrist. Using methods known to those skilled in the art, the first and second images were merged and the merged image is displayed in FIG. 11C. The merged image provides a diagnostic image for viewing a potential secondary tumor site. Note that this image set clearly demonstrates the precision to which the current invention enables the co-location of objects from differing imaging modes. The maximum fluorescent signal emanating from a pre-metastatic tumor on the radius (arm-bone) tip at the wrist is within about 0.1 mm of the suspect lesion subsequently identified by microscopic histology.

Figure 12:
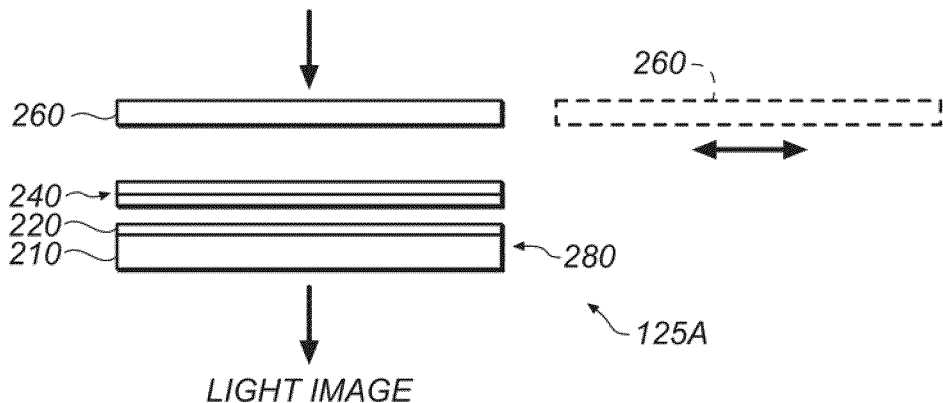
FIG. 12 is a diagrammatic view of a suitable phosphor plate for use with the apparatus and method of the present invention.

A phosphor plate suitable for use with the apparatus and method of the present invention is disclosed in U.S. Pat. No. 6,444,988 (Vizard), commonly assigned and incorporated herein by reference. A phosphor plate as described in Vizard is shown in FIG. 12. A suitable phosphor plate 125A for use with the apparatus and method of the present invention includes a transparent support 210 (such as glass) upon which is coated an interference filter 220 which is a multicoated short-pass filter designed to transmit light at a specified wavelength (and below) and reflect light above that wavelength. Plate 125A also includes a thin phosphor layer 240 and a removable thick phosphor layer 260. Thin phosphor layer 240 is used for high resolution imaging applications of ionizing radiation or for very low energy (self-attenuating) ionizing radiation such as low-energy electrons or beta particles. Thick phosphor layer 260 is used for high energy ionizing radiation that freely penetrates the phosphor. Thick phosphor layer 260 is removable and is shown in FIG. 12 overlaying thin phosphor layer 240. Layer 260 is removable to the position shown in dashed lines out of contact with layer 240.

The phosphor preferably used in phosphor layers 240 and 260 is Gadolinium Oxysulfide: Terbium whose strong monochromatic line output (544-548 nanometers (NM) is ideal for co-application with interference optics. This phosphor has technical superiority regarding linear dynamic range of output, sufficiently "live" or prompt emission and time reciprocity, and intrascenic dynamic range which exceed other phosphors and capture media. This phosphor layer preferably has a nominal thickness of 10-30 micrometers (μm) at 5-20 grams/square foot (g/ft2) of phosphor coverage, optimally absorbing 10-30 Kev x-rays. Thick phosphor layer 260 has a nominal thickness of 100 μm at 80 g/ft2 of phosphor coverage.

The duplex phosphor layers impart flexibility of usage for which the thick phosphor layer 260 may be removed to enhance the spatial resolution of the image. Thin phosphor layer 240 intimately contacts filter 220, whereas thick phosphor layer 260 may be alternatively placed on thin phosphor layer 240.

Interference filter 220 transmits light at 551 NM and below and reflects light above that wavelength. Filter 220 comprises layers of Zinc Sulfide-Cryolite that exhibits a large reduction in cutoff wavelength with increasing angle of incidence. The filter has a high transmission at 540-551 NM to assure good transmission of 540-548 NM transmission of the GOS phosphor. The filter also has a sharp short-pass cut-off at about 553 NM, that blue shifts at about 0.6 NM per angular degree of incidence to optimize optical gain.

Glass support 210 should be reasonably flat, clear, and free of severe defects. The thickness of support 210 can be 2 millimeters. The opposite side 280 of glass support 210 is coated with an anti-reflective layer (such as Magnesium Fluoride, green optimized) to increase transmittance and reduce optical artifacts to ensure that the large dynamic range of the phosphor emittance is captured.

Figure 13:
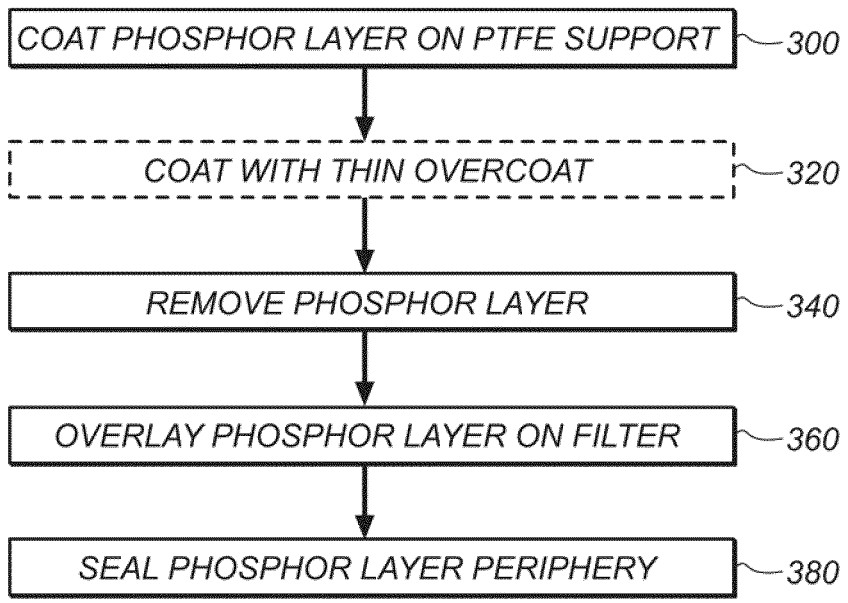
FIG. 13 is a flow diagram of a method for making a phosphor plate of FIG. 12.

FIG. 13 shows steps of a method of producing phosphor layer 240. In step 300, a mixture of GOS:Tb in a binder is coated on a polytetrafluoroethylene (PTFE) support. The PTFE support enables release of the coated phosphor layer from the PTFE support and subsequent use of the phosphor layer without support, since conventional supporting materials are an optical burden to phosphor performance. For the thin phosphor layer 240, at step 320 an ultra thin (about 0.5 g/ft2, 0.5 μm thick) layer of cellulose acetate overcoat can be applied to offer improved handling characteristics of the thin phosphor layer and to provide greater environmental protection to the underlying optical filter. At step 340, the phosphor layer is removed from the PFTE support. At step 360, the thin phosphor layer overcoated side is overlayed on interference filter 220. Clean assembly of the thin phosphor layer 240 and filter 220 assures an optical boundary that optimizes management of phosphor light output into the camera of the lens/camera system. Optical coupling of layer 240 and filter 220 is not necessary, since performance reduction may result. At step 380, layer 240 can be sealed around its periphery and around the periphery of filter 220 for mechanical stability and further protection of the critical optical boundary against environmental (e.g., moisture) intrusion.

Figure 14:
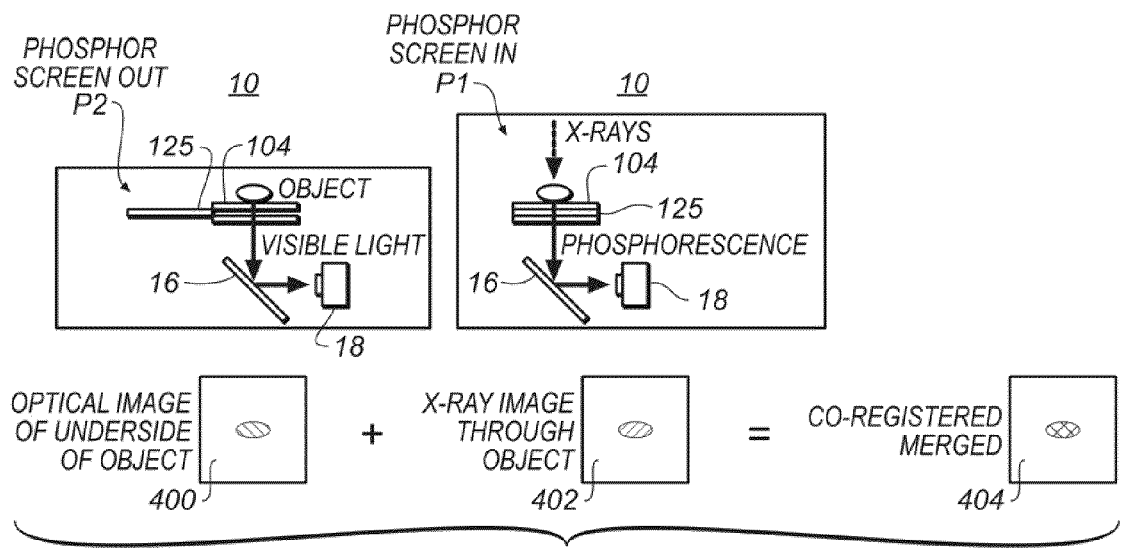
FIG. 14 illustrates schematically how an image captured using the configuration of FIG. 5C can be merged or co-registered with an image captured using the configuration of FIG. 5B.

FIG. 14 illustrates schematically how an image captured using the configuration of FIG. 5C can be merged or co-registered with an image captured using the configuration of FIG. 5B. A first, optical image 400 is acquired of the underside of the object immobilized on sample object stage 104. A second, x-ray image 402 is acquired of the object using x-rays coming from above, as illustrated. Then an image 404 is prepared that co-registers or merges images 400, 402.

Figure 15A:
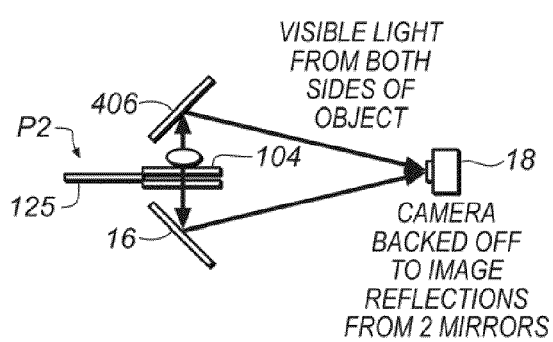
FIG. 15A illustrates schematically a system for capturing visible light images from both sides on an immobilized object.

FIG. 15A illustrates schematically a system for capturing visible light images from both sides of an immobilized object while phosphor plate 125 is in position P2. In addition to a first mirror 16 located beneath sample object stage 104 as illustrated to reflect light from the underside of the object to lens/camera system 18 to capture a first optical image, a second mirror 406 is located on the opposite side or above sample object stage 104 as illustrated to reflect light from the upper side of the object to lens/camera system 18 to capture a second optical image. Preferably, mirror 406 is transparent to x-rays or can be moved by means not illustrated to a position not proximate object stage 104 during x-ray imaging.

Figure 15B:
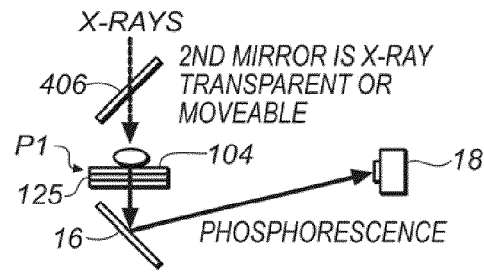
FIG. 15B illustrates schematically how the system of FIG. 15A may be used for capturing an x-ray image from one side of an immobilized object.

FIG. 15B illustrates schematically how the system of FIG. 15A may be used for capturing an x-ray image from one side of an immobilized object while phosphor plate 125 is in position P1. Mirror 406 may be transparent to x-rays or may have been moved aside as previously described. Thus, x-rays pass through the object from above and strike phosphor plate 125, thus causing production of phosphorescence which is reflected by mirror 16 to camera/lens system 18 to capture a first x-ray image. Those skilled in the art will understand that a digital x-ray image captured in this manner using x-rays from above can be processed by control system 20 to produce a second, virtual x-ray image of the object as if x-rays have passed through the object from below. Available software applications for producing such a virtual image include Kodak MI marketed by Carestream Health, Inc.; and ImageJ available from the National Institutes of Health.

Figure 15C:
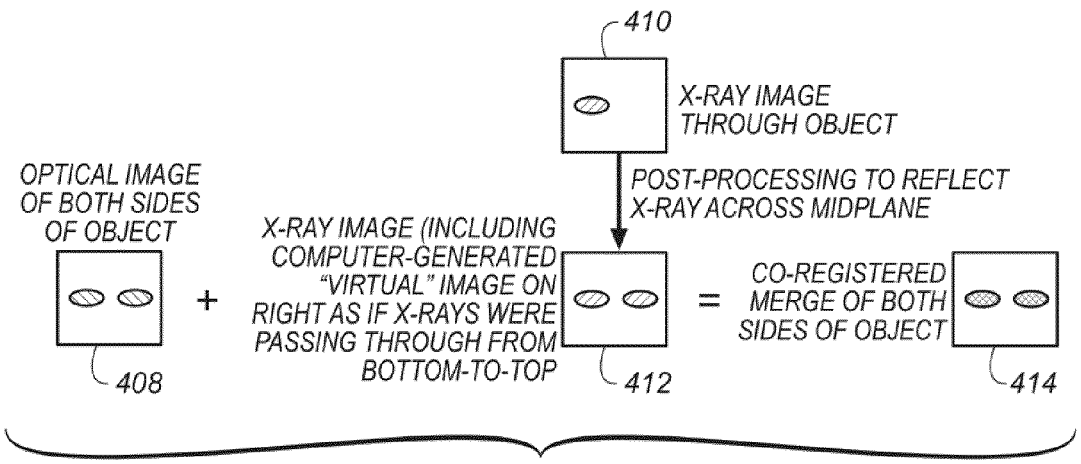
FIG. 15C illustrates how optical images captured as in FIG. 15A may be merged or co-registered with x-ray images captured as in FIG. 15B.

FIG. 15C illustrates how optical images captured as in FIG. 15A may be merged or co-registered with x-ray images captured as in FIG. 15B. An optical image 408 is prepared showing images of both the underside and the upper side of the object on sample object stage 104. An x-ray image 410 is acquired of the object using x-rays from above as illustrated. An x-ray image 412 is prepared showing both image 410 and a virtual image of the object as if x-rays have passed from below. Then an image 414 is prepared that co-registers or merges images of the respective portions of images 408, 412.

Advantages of the present invention include: provides anatomical localization of molecular imaging agent signals in small animals, organs, and tissues; provides precise co-registration of anatomical x-ray images with optical molecular and radio isotopic images using one system; promotes improved understanding of imaging agent's biodistribution through combined use of time lapse molecular imaging with x-ray imaging; and allows simple switching between multi-wavelength fluorescence, luminescence, radio-isotopic, and x-ray imaging modalities without moving the object/sample.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10 electronic imaging system
12 light source
14 optical compartment
16 mirror
18 lens/camera system
20 communication/computer control system
22 monitor
100 imaging system of the present invention
102 x-ray source
104 sample object stage
106 epi-illumination; fiber optics
108 sample environment
110 access means/member
120 frame
122 support sheet
125, 125A phosphor plate
126 optical platen
128 protective layer
130 phosphor layer
132 optical layer
134 support plate; glass
136 air gap/void
138 air gap/void
150, 152, 154, 156 example—potential secondary early detection sites/area.
200-208 method steps
210 transparent glass support
220 interference filter coating
240 thin phosphor layer
260 thick phosphor layer
280 opposite side of 210
300-380 method steps
400 optical image of underside of object
402 x-ray image through object from above
404 co-registered or merged images 400, 402
406 mirror, reflects light, transparent to x-rays
408 optical images of underside and upper side of object
410 x-ray image through object from above
412 image 410 and virtual x-ray image through object from below
414 co-registered or merged images 408, 412
A path of movement of 125
P1 position of 125 proximate 104
P2 position of 125 not proximate 104

What is claimed is:

1. An imaging system for imaging an object, comprising:
a support member adapted to receive the object in an immobilized state;
an imaging unit that images the immobilized object in a first imaging mode to capture a first image, the first imaging mode being selected from the group consisting of: x-ray mode and radio isotope mode, and that images the immobilized object in a second imaging mode that uses light from the immobilized object, different from the first imaging mode, to capture a second image, the second imaging mode being selected from the group consisting of: bright-field mode, fluorescence mode, and luminescence mode;

a movable phosphor plate to transduce ionizing radiation to visible light, the phosphor plate being mounted to be moved, while the object remains immobilized on the support member, between:
a first position proximate the support member for and during capture of the first image; and
a second position not proximate the support member during capture of the second image; and
a capture system that captures either the first image or the second image of the object.

2. The imaging system of claim 1, further comprising an image merging unit that generates a third image by merging the first and second images.

3. The imaging system of claim 1, further comprising multiple optical elements to enable the location of a common focal plane shared by the first and second imaging modes.

4. An imaging system for imaging an object, comprising:
a support member adapted to receive the object in an immobilized state;
an imaging unit that images
the immobilized object in a first imaging mode to capture a first image, the first imaging mode being selected from the group consisting of: x-ray imaging mode and isotope imaging mode, and images
the immobilized object in a second imaging mode that uses light from the object to capture a second image, the second imaging mode being selected from the group consisting of: bright-field imaging mode and dark-field imaging mode;
a movable phosphor plate mounted to be selectively movable between a first position proximate the support member when capturing the first image and a second position not proximate the support member prior to capturing the second image; and
a capture system that captures either the first image or the second image of the object.

5. The imaging system of claim 4, further comprising an image merging unit that generates a third image by merging the first and second images.

6. The imaging system of claim 4, further comprising multiple optical elements to enable the location of a common focal plane shared by the first and second imaging modes.

* * * * *